United States Patent [19]

Herkenrath

[11] 4,064,131

[45] Dec. 20, 1977

[54] PROCESS FOR THE PRODUCTION OF 1,2-DIHYDRO-2-OXO-4-METHYL-7-ACETOACETIC ACID AMIDO-QUINOLINE

[75] Inventor: Erik Herkenrath, Glis, Switzerland

[73] Assignee: Lonza, Ltd., Gampel, Switzerland

[21] Appl. No.: 558,355

[22] Filed: Mar. 14, 1975

Related U.S. Application Data

[62] Division of Ser. No. 507,071, Sept. 18, 1974, abandoned.

[30] Foreign Application Priority Data

Sept. 20, 1973 Switzerland .................. 13492/73
Sept. 20, 1973 Switzerland .................. 13493/73

[51] Int. Cl.$^2$ ............................................. C07D 215/38
[52] U.S. Cl. ............................ 260/287 K; 260/283 SY
[58] Field of Search ....................... 260/283 SY, 287 K

[56] References Cited

U.S. PATENT DOCUMENTS 2,754,293  7/1956  Brody et al. ............... 260/288 R X

OTHER PUBLICATIONS

Boese, "Ind. and Eng. Chem.", vol. 32, pp. 16–22, (1940).

Primary Examiner—Donald G. Daus
Assistant Examiner—D. B. Springer
Attorney, Agent, or Firm—Virgil H. Marsh

[57] ABSTRACT

A process for producing 1,2-dihydro-2-oxo-4-methyl-7-amino-quinoline by reacting one mole of diketene with one mole of m-phenylene diamine. Also, a process for producing 1,2-dihydro-2-oxo-4-methyl-7-acetoacetic acid amido-quinoline by reacting two moles of diketene with one mole of m-phenylene diamine.

8 Claims, No Drawings

PROCESS FOR THE PRODUCTION OF 1,2-DIHYDRO-2-OXO-4-METHYL-7-ACETOACETIC ACID AMIDO-QUINOLINE

This is a division of application ser. no. 507,071, filed Sept. 18, 1974, now abandoned.

BACKGROUND OF THIS INVENTION

1. Field of this Invention

This invention relates to a process for the production of 1,2-dihydro-2-oxo-4-methyl-7-amino-quinoline. This invention also relates to a process for the production of 1,2-dihydro-2-oxo-4-methyl-7-acetoacetic acid amido quinoline.

2. Prior Art 1,2-dihydro-2-oxo-4-methyl-7-amino-quinoline has been produced from m-phenylene diamine and acetoacetic ester by heating at 130° C. for 19 hours in an autoclave- a 45 to 60 percent yield resulted (C. 1938, II, 4240). Nowadays acetoacetic acid ester is obtained most economically from diketene.

BROAD DESCRIPTION OF THIS INVENTION

An object of this invention is to obtain a process for the production of 1,2-dihydro-2-oxo-4-methyl-7-amino-quinoline by the reaction of diketene with m-phenylene diamine. A further object of this invention is to obtain such a process which can be conducted at relatively low temperatures and at atmospheric pressure with increased yields.

Another object of this invention is to obtain a process for the production of 1,2-dihydro-2-oxo-4-methyl-7-acetoacetic acid amido quinoline, characterized by the reaction of diketene with m-phenylene diamine.

Other objects and advantages of this invention will be obvious to one ordinarily skilled in the art from this application.

The first embodiment of this invention involves a process for producing 1,2-dihydro-2-oxo-4-methyl-7-amino-quinoline. The process includes reacting about one mole of diketene with about one mole of m-phenylene diamine. The phrase "about one mole" includes the range of 0.9 to 1.1 mole. Preferably one mole of diketene is reacted with one mole of m-phenylene diamine. In such a case, yields of 70 to 80 percent are obtained.

The reaction can be conducted in water in the presence of a catalytic amount of acetic acid. Preferably the amount of acetic acid present is 10 percent by weight of the mixture of water and acetic acid.

The reaction can be conducted in an organic solvent in the presence of about 5 percent by weight of the mixture of the organic solvent and the acetic acid. That amount of acetic acid is catalytic to the subject reaction. The starting materials are soluble in the organic solvent. Examples of the organic solvent are methanol, butyl acetate, carbon tetrachloride and toluene.

The reaction can also be conducted in glacial acetic acid. The reaction is conducted at a temperature below 100° C. and at about or below atmospheric pressure. Preferably the reaction temperature is between 60° and 65° C. Also, under certain circumstances the reaction can be conducted under reflux (reflux is the highest temperature which should normally be used).

This embodiment of this invention allows the production of 7-amino-lepidene directly from diketene (instead of through acetoacetic ester) using a process which is carried out at considerably lower temperatures than prior process and without pressure, but with better yields.

The second embodiment of this invention involves a process for producing 1,2-dihydro-2-oxo-4-methyl-7-acetoacetic acid amido-quinoline. The process involves reacting about two moles of diketene with about one mole of m-phenylene diamine. The phrase "about one mole" includes the range of 0.9 to 1.1 mole and the phrase "about two moles" includes the range of 1.9 to 2.1 moles. Preferably two moles of diketene is reacted with one mole of m-phenylene diamine. In such a case, better results are obtained.

The reaction can be conducted in water in the presence of a catalytic amount of acetic acid. Preferably the amount of acetic acid present is 10 percent by weight of the mixture of water and acetic acid.

The reaction can be conducted in an organic solvent in the presence of about 5 percent by weight of the mixture of the organic solvent and the acetic acid. That amount of acetic acid is catalytic, to the subject reaction. The starting materials are soluble in the organic solvent.

The reaction can also be conducted in glacial acetic acid.

The reaction is conducted at a temperature below 100° C. and at about or below atmospheric pressure. Preferably the reaction temperature is between 60° and 65° C. Also, the reaction can be conducted under reflux (reflux is the highest temperature which should normally be used).

DETAILED DESCRIPTION OF THIS INVENTION 1,2-dihydro-2-oxo-4-methyl-7-amino-quinoline is also termed 7-amino-2-oxy-lepidine or 7-amino-lepidone. 7-amino-lepidone is a intermediate from which valuable pharmaceuticals are and can be made.

1,2-dihydro-2-oxo-4-methyl-7-acetoacetic acid amido-quinoline is also termed 7-acetoacetylamino-4-methyl-quinolone-(2) or 7-acetoacetylamino-lepidone. 7-acetoacetylamino-lepidone is an intermediate from which special pigments are and can be made.

All, parts, ratios, percentages and proportions herein are on a weight basis, unless otherwise stated or obvious to one ordinarily skilled in the art from this disclosure.

EXAMPLE 1

This example is the preferred mode of the first embodiment of this invention.

43.2 gm. of at least 98 percent pure 1,3-phenylene diamine (melting point: 60° to 62° C) and 100 ml of 10 percent acetic acid are placed in a sulfurizing flask equipped with an anchor bolt, reflux cooler, dripping funnel, thermometer and water bath. 35.2 gm. of diketene were allowed to drip into the reaction mixture over the course of about 20 minutes at room temperature. The reaction mixture was stirred during the addition. The temperature was allowed to rise with the aid of the reaction heat to 60° to 65° C. After completion of the addition of diketene, the reaction was allowed to continue for another hour at 60° to 65° C. After cooling to about 15° C. the resultant precipitate was separated out and dried under vacuum at 60° to 70° C until the precipitate reached a constant weight. 49.2 gm. of yellow, discolored 1,2-dihydro-2-oxo-1-methyl-7-amino-quinoline with a melting point of 268° to 269° C were obtained, which corresponded to a yield of 70.7 percent, based on the m-phenylene diamine. After a single recrystallization from dimethylformamide/H₂O (1:1), the product was colorless and had a melting point of 274.6° to 275.4°C.

The example was repeated, except that the single recrystallization was done using 50 percent acetic acid. The product was colorless and had a melting point of 274.0° to 274.8° C.

EXAMPLE 2

This example is the preferred mode of the second embodiment of this invention.

129.6 gm of at least 98 percent pure 1,3-phenylene diamine (melting point: 60° to 62° C) and 750 ml of 10 percent acetic acid were placed in a sulfurizing flask, equipped with an anchor bolt, reflux cooler, drip funnel, thermometer and water bath. 211.2 gm of diketene were allowed to drip into the reaction mixture over the course of 1.5 hours at room temperature. The reaction was stirred during the addition. The temperature, with the aid of the reaction heat, was allowed to rise to 60° to 65° C. After completion of the addition of diketene, the mixture was allowed to continue for another hour at 60° to 65° C. and was then cooled to about 15° C. The precipitated product was then separated out and dried under vacuum at 60° to 70° C. until the precipitate reached a constant weight. 257 gm. of raw, almost colorless, 1,2-dihydro-3oxo-4-methyl-7-acetoacetamido-quinoline was obtained having a melting point of about 238° C. This corresponded to a yield of about 83 percent, based on the m-phenylene diamine. After a single recrystallization from 67 percent acetic acid, the product had a melting point of 246.0° to 247.0° C. After one more recrystallization from the diluted acetic acid, the melting point was found not to have changed.

What is claimed is:

1. The process for producing 1,2-dihydro-2-oxo-4-methyl-7-acetoacetic acid amido-quinoline which comprises the step of reacting diketene with m-phenylene diamine, whereby said 1,2-dihydro-2-oxo-4-methyl-7-acetoacetic acid amido-quinoline results, the molar ratio of diketene to m-phenylene diamine being between 1.77 to 1 and 2.33 to 1 the reaction being conducted (i) in water in the presence of a catalytic amount of acetic acid or (ii) in an inert organic solvent in the presence of a catalytic amount of acetic acid, the reactants being soluble in the organic solvent, or (iii) in glacial acetic acid, the reaction being conducted at a temperature between room temperature and reflux temperature, and the reaction being conducted at atmospheric pressure.

2. The process as described in claim 1 wherein two moles of said diketene are reacted with one mole of said m-phenylene diamine.

3. The process as described in claim 1 wherein the reaction is conducted in water in the presence of a catalytic amount of acetic acid.

4. The process as described in claim 3 wherein the acetic acid is 10 percent by weight of the mixture of water and acetic acid.

5. The process as described in claim 1 wherein the reaction is conducted in an organic solvent in the presence of about 5 percent by weight of the mixture of the organic solvent and the acetic acid, that amount of acetic acid being catalytic, and the starting materials being soluble in the organic solvent.

6. The process of claim 1 wherein the reaction is conducted in glacial acetic acid.

7. The process of claim 1 wherein the reaction is started at room temperature and is continued at a temperature between 60° and 65° C.

8. The process of claim 1 wherein the reaction is conducted under reflux.

* * * * *